(12) United States Patent
Rajagopal et al.

(10) Patent No.: US 8,356,763 B2
(45) Date of Patent: Jan. 22, 2013

(54) MECHANICAL LYSIS ARRANGEMENTS AND METHODS

(75) Inventors: Aditya Rajagopal, Irvine, CA (US); Axel Scherer, Laguna Beach, CA (US); Mladen Barbic, Sterling, VA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 13/427,672

(22) Filed: Mar. 22, 2012

(65) Prior Publication Data

US 2012/0175441 A1     Jul. 12, 2012

Related U.S. Application Data

(62) Division of application No. 12/554,817, filed on Sep. 4, 2009, now Pat. No. 8,201,765.

(60) Provisional application No. 61/191,344, filed on Sep. 8, 2008.

(51) Int. Cl.
B02C 17/10 (2006.01)
(52) U.S. Cl. .......................................................... 241/2
(58) Field of Classification Search ............... 241/2, 172
See application file for complete search history.

(56) References Cited

U.S. PATENT DOCUMENTS

| | | |
|---|---|---|
| 2,350,534 A | 6/1944 | Rosinger |
| 3,172,546 A | 3/1965 | Schreiner |
| 3,987,967 A | 10/1976 | Kuznetsov et al. |
| 4,134,557 A | 1/1979 | Lazzari et al. |
| 4,676,439 A | 6/1987 | Saito et al. |
| 5,377,917 A | 1/1995 | Wiljan et al. |
| 5,516,670 A | 5/1996 | Kuehnle et al. |
| 5,921,477 A | 7/1999 | Tomes et al. |
| 6,719,610 B2 | 4/2004 | Chou et al. |
| 6,880,771 B2 | 4/2005 | Deppermann |
| 8,201,765 B2 | 6/2012 | Rajagopal et al. |
| 2005/0258288 A1* | 11/2005 | Dalziel et al. ............. 241/172 |

OTHER PUBLICATIONS

Restriction Requirement mailed on Dec. 28, 2012 for U.S. Appl. No. 12/554,817, filed Sep. 4, 2009 in the name of Aditya Rajagopal et al.
Ex-Parte Quayle Action mailed on Mar. 9, 2012 for U.S. Appl. No. 12/554,817, filed Sep. 4, 2009 in the name of Aditya Rajagopal et al.
Notice of Allowance mailed on Apr. 12, 2012 for U.S. Appl. No. 12/554,817, filed Sep. 4, 2009 in the name of Aditya Rajagopal et al.

* cited by examiner

*Primary Examiner* — Mark Rosenbaum
(74) *Attorney, Agent, or Firm* — Steinfl & Bruno, LLP (57) ABSTRACT

Methods and arrangements to lyse a biological sample are described. The arrangements comprise a lysis tube containing the sample, one or more electromagnets generating a magnetic field, and one or more permanent magnets inside the lysis tube. The permanent magnets move and lyse the sample when a magnetic field is generated by the electromagnets.

7 Claims, 11 Drawing Sheets

FIG. 11 ously more important in bio-technology and medical diagnostics.

MECHANICAL LYSIS ARRANGEMENTS AND METHODS

CROSS REFERENCE TO RELATED APPLICATIONS

This application is a divisional of prior U.S. application Ser. No. 12/554,817 filed on Sep. 4, 2009, which claims priority to U.S. provisional application Ser. No. 61/191,344, filed on Sep. 8, 2008 entitled "Portable magnetically motivated mechanical lysis device", and is incorporated herein by reference in its entirety.

FIELD

The present disclosure relates to arrangements and methods for mechanical lysis, fracturing, crushing, and compressing of objects such as biological samples.

BACKGROUND

Biological assay systems are becoming increasingly more important in bio-technology and medical diagnostics. A useful biological agent detection method is using DNA or RNA detection of an organism through a polymerase chain reaction (PCR), real-time polymerase chain reaction (RT-PCR), or reverse-transcriptase polymerase chain reaction. Alternatively, assaying for the presence of a particular cellular protein can also be used to detect or study biological samples of interest. Before a cell or environment sample can be analyzed using PCR or protein analysis for example, it must first be prepared for analysis. A challenge in biological sample preparation is lysis of the cell membrane and, if present, the cell wall.

Common lysis techniques comprise at least three categories: chemical lysis, mechanical, lysis, and thermal lysis. Chemical lysis involves exposing the biological sample of interest to a cocktail of solvents and harsh chemicals that promote the degeneration of the cell membrane. This permits easy access to the biological sample's genetic material, intracellular proteins or cellular lipids. Although chemical lysis can be effective, each chemical cocktail needs to be tailored to the organism of interest. This requires that the chemical cocktail be completely redesigned to perform lysis on a different biological sample.

A second method of lysis is thermal lysis. Heating cells to a high temperature causes cellular protein denaturation and cell membrane breakdown. This method is not ideal when the goal is to assay for relatively rare DNA, RNA or protein targets, as the harsh process of thermal lysis may destroy the target to be detected.

A third approach to cell lysis is mechanical lysis. This method uses a crushing or grinding action to cleave cell membranes. For example, glass beads can be centrifuged along with the sample at a high angular velocity, cleaving cells as they grind past each other. Some centrifuge systems also rock the sample using three dimensional movements to increase the efficiency of lysis. Another method of mechanical lysis is to pressure the cell sample and flow it past a piercing object at a high velocity. This however requires a significant amount of external equipment such as expensive and bulky vacuum pumps. There is a need, therefore, for a more compact mechanical cell lysis solution.

SUMMARY

Provided herein are arrangements and methods for mechanical lysis, fracturing, crushing, and compressing of objects such as biological samples.

According to a first aspect, a mechanical lysis arrangement is provided, comprising a lysis tube for containing a biological sample during lysis, at least one electromagnet, the at least one electromagnet generating a magnetic field when electric current is passed therethrough, at least one permanent magnet located inside the lysis tube, the at least one permanent magnet sized to be substantially restricted to motion along an axis the lysis tube, the motion occurring when a magnetic field is generated by the at least one electromagnet during operation of the arrangement.

According to a second aspect, a method to lyse a biological sample is provided, comprising placing the biological sample and at least one permanent magnet inside a lysis tube, and generating a magnetic field, the magnetic field accelerating the at least one permanent magnet towards the biological sample for a time and under conditions sufficient to cause the biological sample to be lysed.

The details of one or more embodiments of the disclosure are set forth in the accompanying drawings and the detailed description and examples below. Other features, objects, and advantages will be apparent from the detailed description, examples and drawings, and from the appended claims.

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

FIG. 11 shows a micrograph depicting results of cell lysis experiments using several methods of lysis. Panel A shows a micrograph of yeast cells from a stock solution, wherein the cells did not undergo any method of cell lysis. Panel B shows a micrograph depicting results of a cell lysis experiment using the mechanical lysis arrangement according to several embodiments, wherein the experiment was conducted for 15 minutes continuously without interruption. Panel C shows a micrograph depicting results of a cell lysis experiment using the mechanical lysis arrangement according to several embodiments, wherein the experiment was conducted for 15 minutes using a pulsed protocol. Panel D shows a micrograph depicting results of a cell lysis experiment using an alternative, commercially available method of cell lysis.

DETAILED DESCRIPTION

Provided herein are arrangements and methods for mechanical lysis, fracturing, crushing, and compressing of objects such as biological samples.

The term "lysis" or "lyse" as used herein indicates disrupting a biological sample in order to gain access to materials that are otherwise inaccessible. When the biological sample is a living cell, lysis refers to causing the death of the cell by breaking of the cellular membrane, causing the contents to spill out. In particular, methods of lysis include, but are not limited to, chemical lysis, thermal lysis, mechanical lysis, and osmotic lysis. Lysis of cells or other biological samples is useful for analysis of such things as DNA, RNA, proteins or lipids. For example, one may wish to lyse a blood cell from a forensic blood sample in order assay the DNA of that cell. The term "lysate" as used herein indicates a liquid or solid collection of materials following a lysis procedure.

The term "biological sample" as used herein indicates any object, living or dead, that one wishes to lyse in order to gain access to materials that would not be accessible without lysis. In particular, biological samples comprise individual cells or more complicated collections of cells such as those found in tissues or existing in the environment. Biological samples can be a liquid phase solution of cells or it may be a solid cell sample such as a cell pellet derived from a centrifugation procedure. Exemplary biological samples include blood, urine, laboratory cell samples, environmental samples, and forensic samples.

Figure 1:
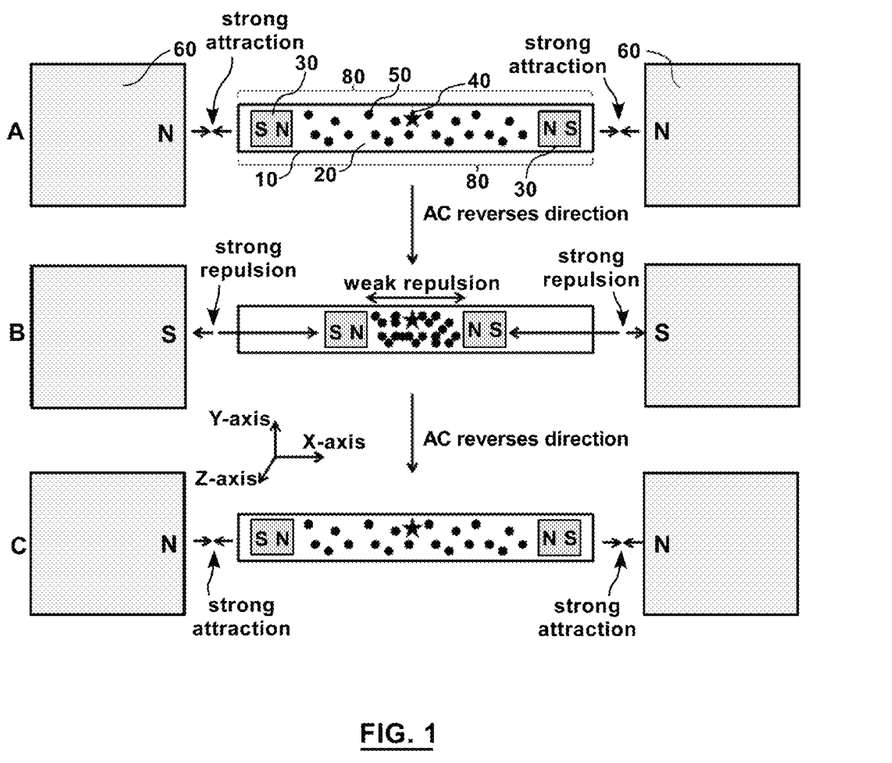
FIG. 1 shows a schematic of a mechanical lysis arrangement according to several embodiments of the present disclosure. In the embodiment shown, the arrangement comprises two electromagnets, a lysis tube containing several lysis aids, two permanent magnets, and a biological sample.

In several embodiments, a mechanical lysis arrangement configured to lyse a biological sample is provided. The mechanical lysis arrangement comprises a lysis tube for containing the biological sample during a lysis procedure. FIG. 1 shows a schematic illustration of the mechanical lysis arrangement.

The term "lysis tube" as used herein indicates a tube forming a chamber wherein lysis of a biological sample takes place. The term "lysate" indicates the material formed by lysis of the biological sample. As shown in FIG. 1, lysis tube (10) is closed or otherwise sealed to prevent leakage of the lysate and/or the biological sample (40) from the chamber (20). For example, lysis tube (10) can be a laboratory test tube such as a 0.65 mL or 1.5 mL minicentrifuge tube. In other embodiments, lysis tube (10) can be a 15 mL or 50 mL laboratory tube. In yet other embodiments, a lysis tube (10) may be a single PCR tube, a PCR tube among a plurality of attached PCR tubes, or a well among a plurality of wells in a 96 or 384 well plate.

Figure 2:
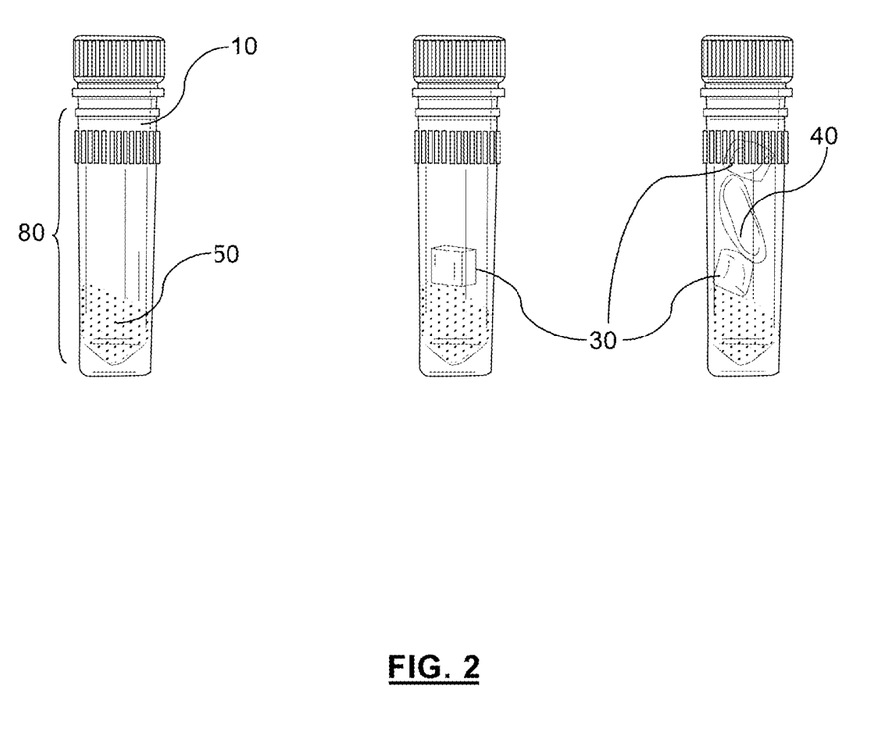
FIG. 2 shows several lysis tubes to be used in connection with the mechanical lysis arrangement according to several embodiments of the present disclosure. The left tube is filled approximately 20% (by volume) with 100 μm glass beads. The center tube is filled approximately 20% (by volume) with 100 μm glass and a NeFeB permanent magnet. The right tube is filled approximately 20% (by volume) with 100 μm glass beads, and two NeFeB permanent magnets flanking a biological sample (e.g., a coffee bean) on both sides.

In several embodiments, as also shown in FIG. 2, a lysis tube (10) comprising a laboratory test tube is sealed with a push or screw cap, whereas a lysis tube (10) comprising a well of a plurality of wells in a plate format is sealed with an adhesive material. FIG. 2 shows a photograph of several lysis tubes (10) comprised of a laboratory test tube filled with a variety of components.

The mechanical lysis arrangement of several embodiments further comprises at least one electromagnet (60) (FIG. 1) for generating a magnetic field when electric current is passed through a wire coil (not shown) of the electromagnet (60).

The term "magnet" as used herein indicates an object or material that produces a magnetic field. In particular, magnets include permanent magnets and electromagnets. The term "permanent magnet" as used herein indicates a magnet made from a material that stays magnetized. Exemplary materials that can be used to make a permanent magnet include iron, nickel, cobalt, rare earth metals and some of their alloys (e.g. Alnico), and some naturally occurring minerals such as lodestone. The term "electromagnet" as used herein indicates an arrangement made from a coil of wire which acts as a magnet when an electric current passes through it, but stops being a magnet when the current stops. Often an electromagnet is wrapped around a core of ferromagnetic material like steel, which enhances the magnetic field produced by the coil. The term "ferromagnetic" as used herein indicates a material that exhibits spontaneous magnetism.

In several embodiments, the mechanical lysis arrangement comprises two electromagnets (60) arranged in opposition to one another (FIG. 1). The electromagnet (60) or electromagnets (60) of the mechanical lysis arrangement are typically capable of producing a magnetic field of between 0.003 Tesla and 5 Tesla when current is passed through the electromagnet wire coil. The electromagnets (60) can be powered by a variety of means, including direct current (DC) or alternating current (AC). AC current is typically passed through the electromagnet coils using wall outlet AC of 120 volts and 60 Hz (sine wave), but virtually any AC source can be used as an alternative so long as the electromagnet (60) does not overheat. If either AC or DC is used to power the electromagnets (60), the current can be operated with a manual switch or more complex electronics, known and understood by those with skill in the art, which can allow for more complex patterns of current to be passed through the electromagnets (60) and therefore vary the strength and direction of the magnetic field over time.

The mechanical lysis arrangement according to the present disclosure further comprises at least one permanent magnet (30) (FIG. 1). In several embodiments, the arrangement comprises at least two permanent magnets (30). The permanent magnet or magnets (30) are located inside the lysis tube (10). Furthermore, the permanent magnet or magnets (30) are sized such that their motion is restricted by the sidewalls of the lysis tube (10), allowing the permanent magnet or magnets (30) to move substantially only in a linear direction along an axis, e.g., the X-axis of the lysis tube (10). The X, Y, and Z axes of the lysis tube (10) in relation to the electromagnets (60) and permanent magnets (30) are defined in FIG. 1, Panel C. The sidewalls (80) of the lysis tube (10) prevent the permanent magnet or magnets (30) from rotating when the direction of the magnetic field of the electromagnets (60) is reversed during passage of alternating current through the electromagnet (60). Therefore, in the embodiment according to FIG. 1, restriction of motion of the permanent magnet or magnets (30) occurs by configuring the sidewalls (80) and/or the permanent magnet or magnets (30) to allow movement substantially along a linear direction.

FIG. 2 shows an example of a lysis tube (10) comprised of a laboratory test tube wherein two permanent magnets (30) and an exemplary biological sample (40) (e.g., a coffee bean) are located therein.

Figure 3:
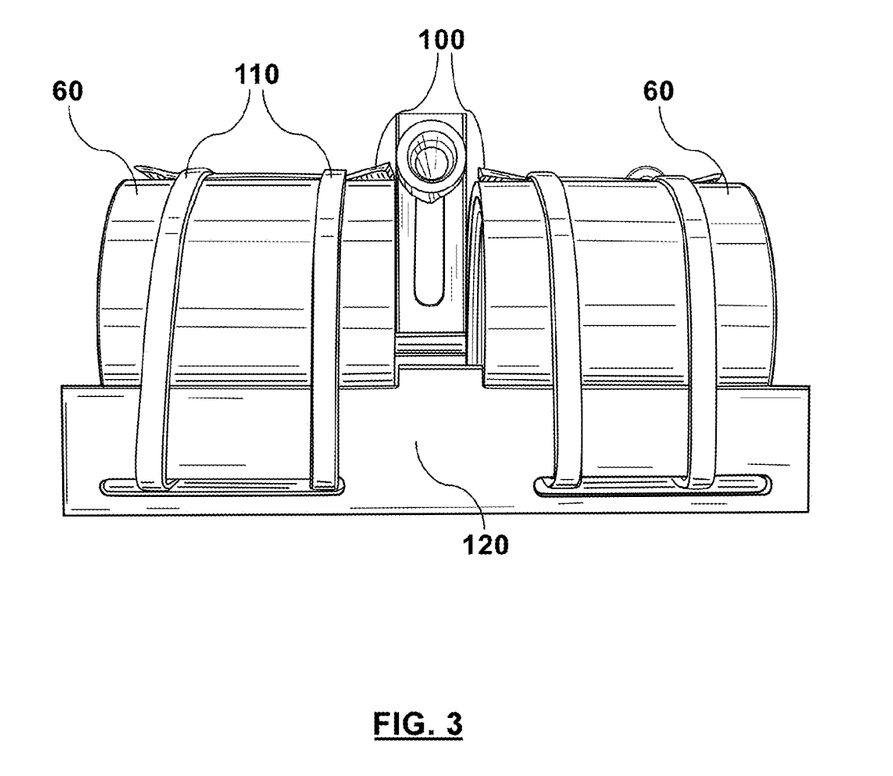
FIG. 3 shows a front view of a mechanical lysis arrangement.

According to some embodiments of the present disclosure, the mechanical lysis arrangement can further comprise a bracket (120) (FIG. 3). The bracket (120) can be made of metal such as aluminum, plastic, or another suitable material. The bracket (120) is configured to attach with the at least one electromagnet (60). For example, the bracket (120) can attach with the electromagnets (60) by way of nylon clamps (110).

Figure 4:
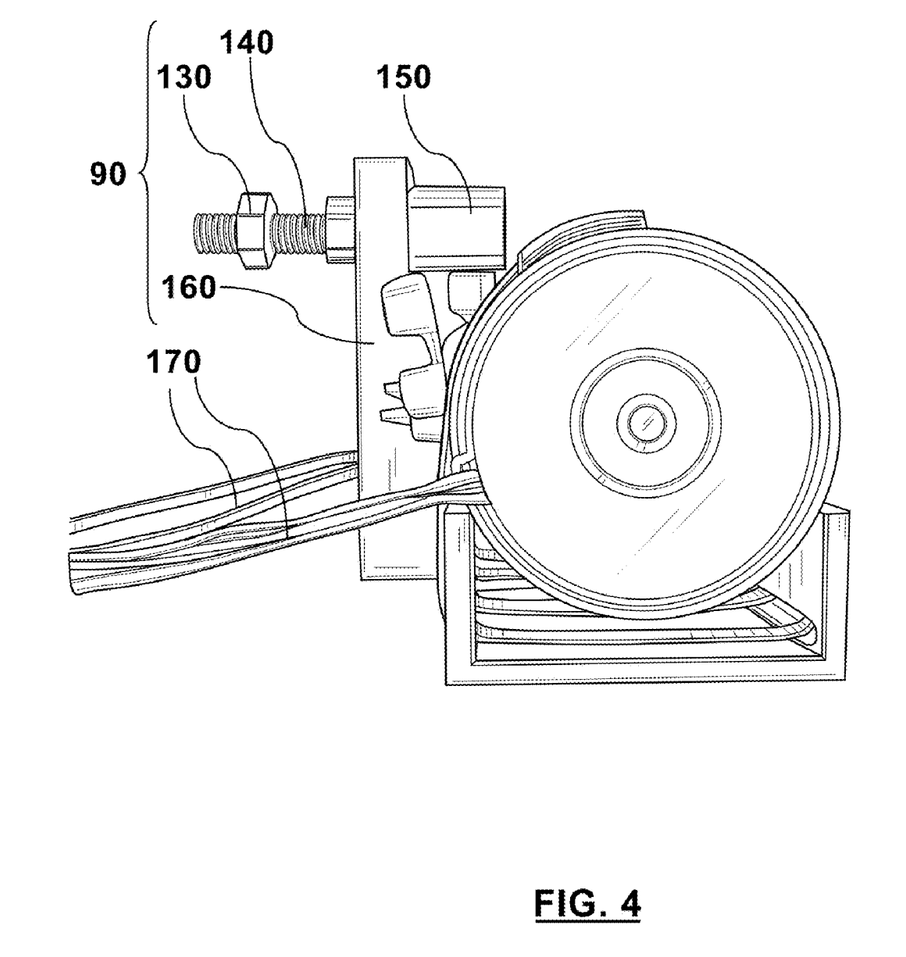
FIG. 4 shows a side view of the arrangement of FIG. 3.
Figure 5:
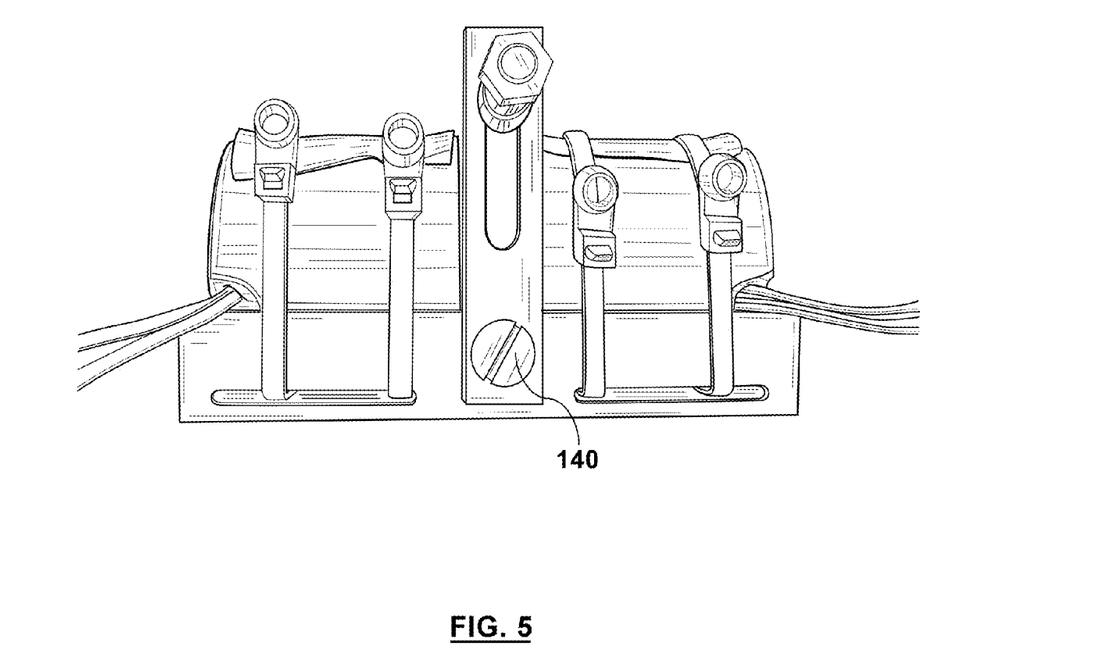
FIG. 5 shows a rear view of the arrangement of FIG. 3.

When nylon clamps (110) are used, it is useful in several embodiments to further secure the electromagnets (60) of the mechanical lysis arrangement by using a set of rubber sheets (100) between the electromagnet (60) surface and each nylon clamp (110). Alternatively, as shown in FIG. 4, the bracket (120) can attach with the electromagnets (60) using a bolt (140) and nut (130) arrangement, by adhesive means or by other means not disclosed but understood by those with skill in the art. Further, the bracket (120) can function to support the mechanical lysis arrangement and impart a flat bottom surface to the mechanical lysis arrangement that facilitates use of the mechanical lysis arrangement on a flat surface such as a table or a laboratory bench-top. For example, FIGS. 3-9 demonstrate an embodiment of the mechanical lysis arrangement comprising a bracket, the arrangement situated on a flat surface.

In several embodiments, the mechanical lysis arrangement further comprises a receptacle (90) (FIG. 4). The receptacle (90) is configured to support the lysis tube (10) and to allow the lysis tube (10) to be suitably positioned during operation of the arrangement. The receptacle (90) is preferably made of a non-metallic material such as plastic or Teflon® so as not to be interfered with by the magnetic fields generated by the magnets of the mechanical lysis arrangement.

Turning to the diagram of FIG. 1, in several embodiments, the mechanical lysis arrangement further comprises a plurality of lysis aids (50) (FIGS. 1-2). The term "lysis aid" as used herein indicates a particle that is suitable to aid in causing lysis of the biological sample (40) during operation of the mechanical lysis arrangement. In particular, the plurality of lysis aids (50) are located inside the lysis tube (10) and come into physical contact with the biological sample (40) during lysis, facilitating the process of lysis. Particles suitable to be lysis aids (50) are glass/silica beads, graphite or iron filings, plastic beads, or other metal particles. Lysis aids (50) can be diamagnetic or not magnetic in any way. Glass beads are most often used as lysis aids (50). In several embodiments, lysis aids (50) can range in size from 0.1 μm to 1000 with an optimal range being approximately 50 to 500 μm for glass beads.

With continued reference to FIG. 1, operation of the arrangement involves loading one or more permanent magnets (30), a plurality of lysis aids (50), and a biological sample (40) to be lysed into the lysis tube (10). FIG. 1 shows a schematic representation of operation of the mechanical lysis arrangement according to several embodiments. Panel A depicts an illustration of the arrangement described in the first sentence of the present paragraph. Under these circumstances, the direction of the magnetic field of the electromagnets (60) causes the permanent magnets (30) to be attracted to the electromagnets (60). When, for example, AC reverses direction and the magnetic field direction reverses (Panel B), the permanent magnet (30) are repelled from the closer electromagnet (60) and toward the center of the lysis tube (10). This movement forces the permanent magnets (30) into the lysis aids (50) with a considerable amount of force. This force causes the biological sample (40) (e.g. a biological cell) to shear against the lysis aids (50). Panel C depicts the state of the arrangement following another reversal of the AC direction, bringing it back to the same direction as illustrated in Panel A. Mechanical lysis is achieved through a repeated movement of the permanent magnets (30) back and forth within the lysis tube (10) during, for example, a 60 Hz AC current.

An exemplary mechanical lysis arrangement was built and tested. The tested arrangement comprises a lysis tube (10) according to FIG. 2, wherein a laboratory test tube (10) (FIG. 2) of 2.5 mL was used. Neodymium Iron Boron (NeFeB) alloy magnets (30) (FIG. 2) were used as permanent magnet (30) (rated at 0.3 Tesla at the surface). The lysis tube (10) was filled with 500 μm glass beads to be used as lysis aids (50) (FIG. 2). In one test of the arrangement, a biological sample (40) comprising a coffee bean was tested (FIG. 2).

Figure 6:
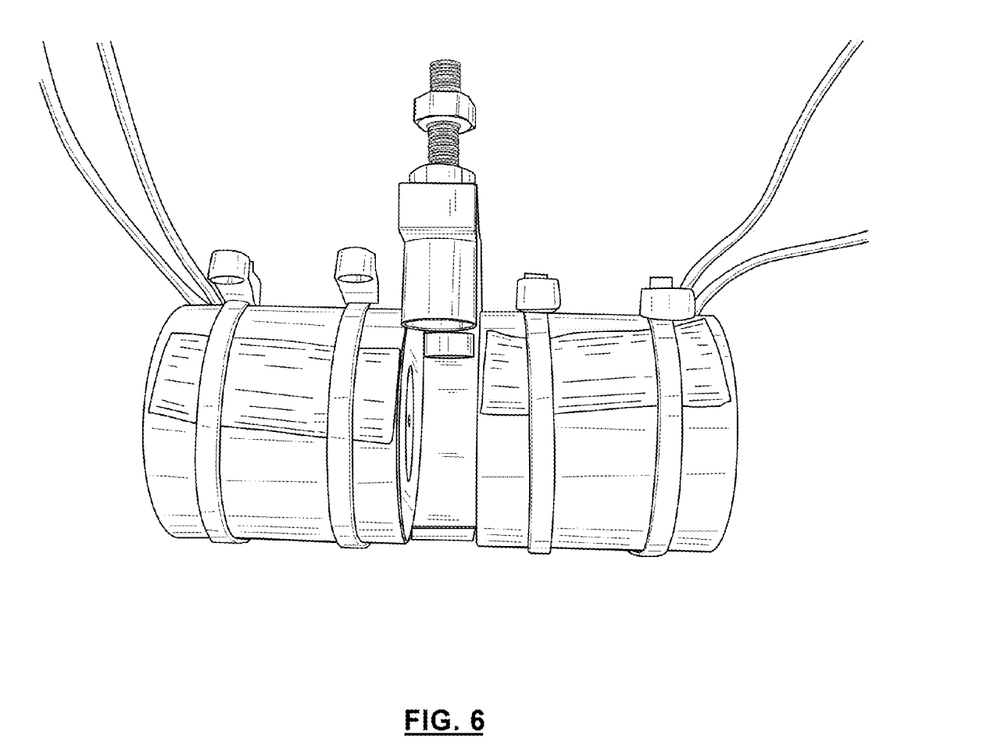
FIG. 6 shows a top perspective view of the arrangement of FIG. 3.
Figure 7:
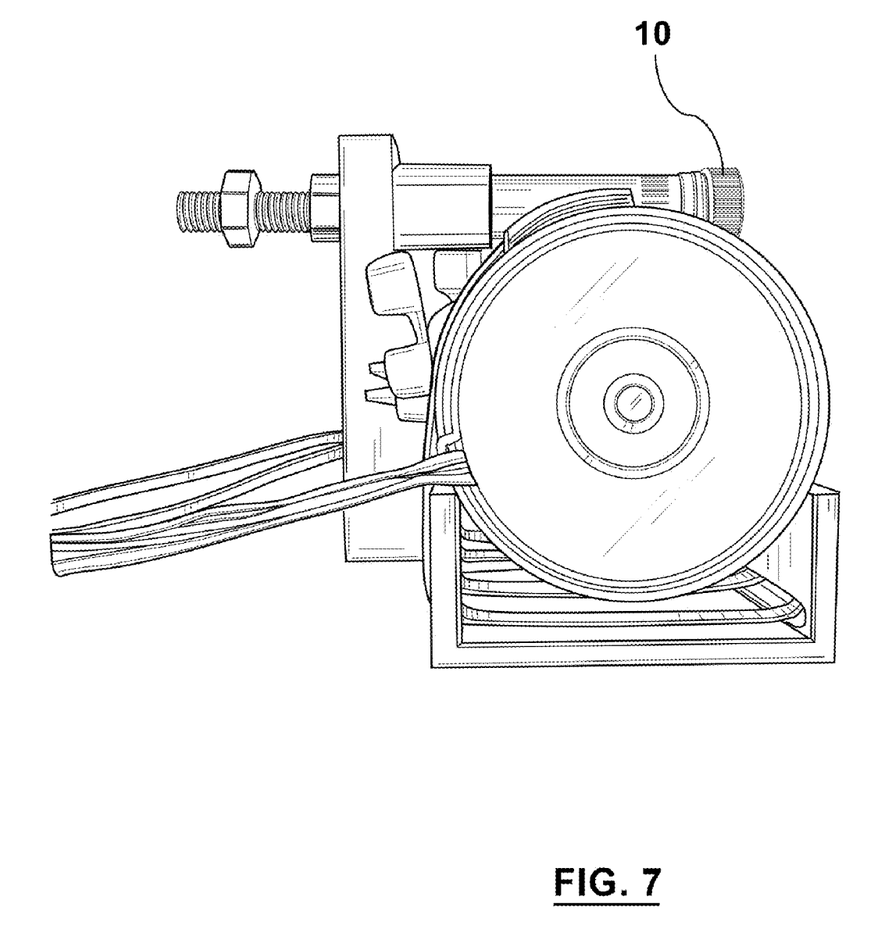
FIG. 7 is similar to FIG. 4, with a centrifuge tube inserted in a tube receptacle.

The centrifuge tube/lysis tube (10) was affixed to an adjustable Teflon® receptacle (90). The receptacle (90) comprises a tube holder (150) (FIG. 4) for holding the lysis tube (10), a bolt (140) (FIG. 4) for holding the tube holder (150), a nut (130) (FIG. 4) for tightening and loosening the bolt (140), a pillar (160) (FIG. 4) for holding the lysis tube (10) in a variety of positions relative to the electromagnets (60), a second bolt (140) (FIG. 5) for securing the pillar (160) to a bracket (120), and an unpictured nut (130) for tightening the bolt (140) (FIG. 5) to a metal bracket (120). This receptacle (90) was then mounted on the bracket (120) (FIG. 3). Two electromagnets (60) (rated at 140 pounds lifting force with the application of 24 volts DC) were mounted onto the bracket (120) and secured using nylon clamps (110). Each magnet is powered through a power cord (170) (FIG. 4) by a sinusoidal current source rated at 120 volts and 60 Hz. FIG. 6 and FIG. 7 show additional views of the mechanical lysis arrangement. FIG. 7 shows the same view as FIG. 4 but with a lysis tube (10) loaded into the tube holder (150).

Figure 8:
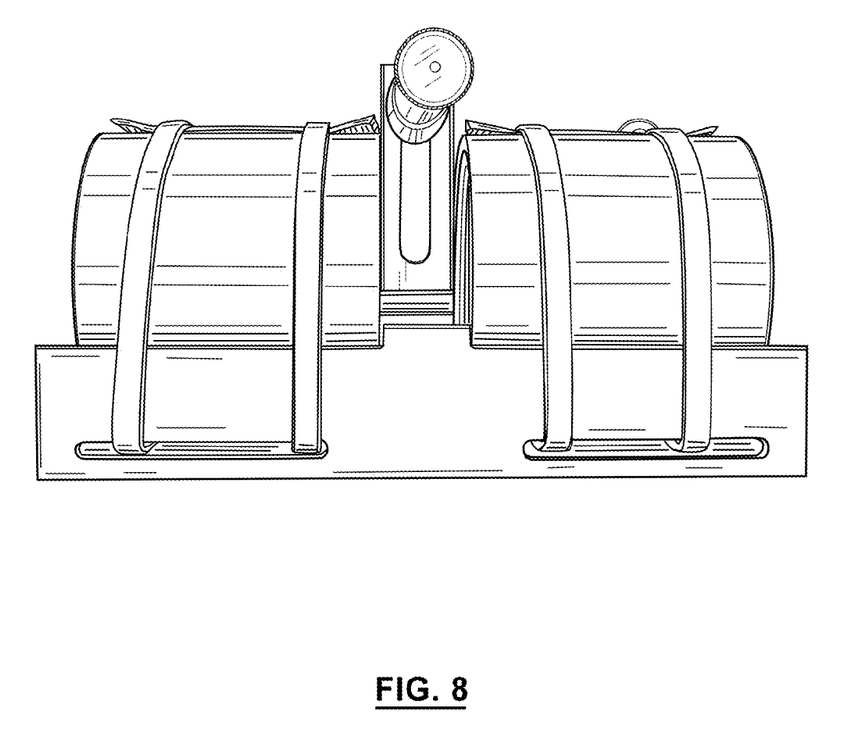
FIG. 8 is similar to FIG. 3, with a centrifuge tube inserted in a tube receptacle.
Figure 9:
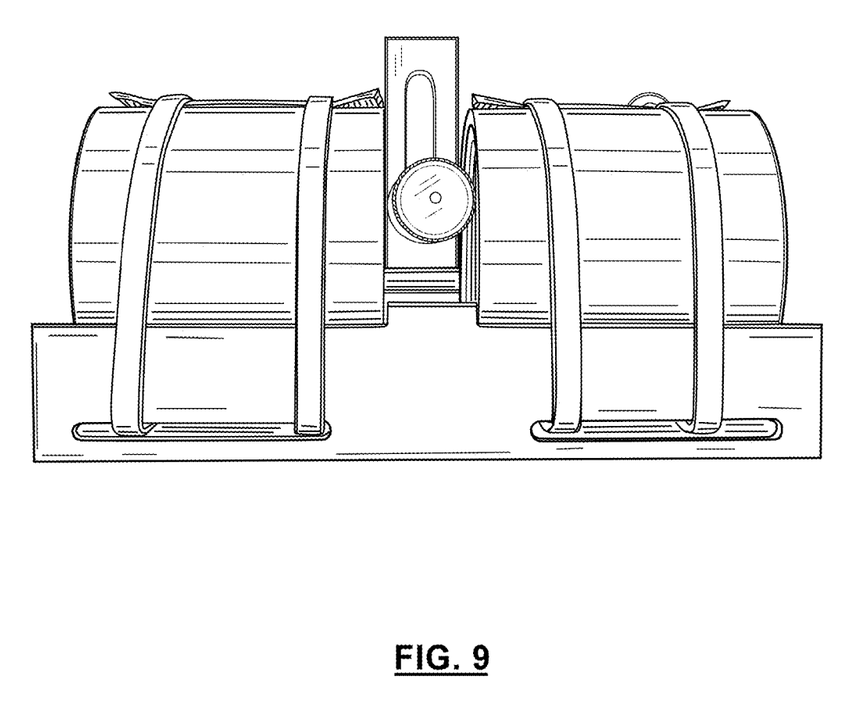
FIG. 9 is similar to FIG. 3, with a centrifuge tube inserted in a tube receptacle, the tube being in a different position than that shown in FIG. 8.

During operation, the lysis tube (10) is lowered from its position as depicted in FIG. 8 to its position as depicted in FIG. 9 such that is situated between the north and south poles of the electromagnets (60). When alternating current is applied to the electromagnets (60), a magnetic field of approximately 0.3 Tesla is generated in the vicinity of the centrifuge tube. Since the current source is sinusoidal, this creates a time-varying magnetic field that switches polarity at the rate of 60 Hz. In turn, this causes the NeFeB permanent magnet (30) to be alternately attracted and repulsed by the magnet field (as illustrated schematically in FIG. 1). Since the centrifuge tube is confined by the centrifuge tube to specific dimensions in the Z-axis, this attractive/repulsive force is converted to a translative or reciprocating movement along the X-axis (axes illustrated and defined in FIG. 1).

Examples 1 and 2, later discussed, describe experimental testing of the particular mechanical lysis arrangement according to FIGS. 3-9.

A variety of different embodiments of the invention of the present disclosure are possible when particular parameters of the arrangement are varied according to the needs of the user. For example, for particular biological samples (40) it may be useful to increase or decrease the rate at which the permanent magnets (30) are moved back and forth within the lysis tube (10). This can be accomplished by increasing or decreasing the AC alternation rate. The AC alternation rate that one will want to use is between about 1 kHz and 1 Hz.

Further, the permanent magnet (30) material can be varied to arrive at permanent magnets (30) with varying properties. For example, more fragile biological samples (40) may be better suited for a permanent magnet (30) with a weaker magnetic strength whereas a more robust sample may be better suited for a permanent magnet (30) with a strong magnetic field.

Lysis tube (10) size and dimensions can be varied depending on the needs of the user. For example, to lyse samples that are larger than those that will fit within the tubes as depicted in FIG. 2, a larger lysis tube (10) should be used. In some cases when a larger lysis tube (10) is used it will be necessary to correspondingly increase the size of the electromagnet (60) of the arrangement, or at least increase the width of the iron core within the electromagnet (60).

Although the lysis tube (10) should be as close as possible to the surface of the iron core of the electromagnet (60), the distance can be varied slightly and still allow for efficient lysis of the biological sample (40). In addition, although the position of the lysis tube (10) of the arrangement should be as close to centered on the iron core of the electromagnet (60) as possible, the distance away from this centered position can be varied slightly and still allow for efficient lysis of the biological sample (40).

The dimensionality, spacing, and the arrangement of the magnetic sources (e.g. the electromagnets) can be tailored to the specific lysis application. For example, the electromagnets may consist of a compact-diameter, tightly wound coil in order to maximize the magnetic field strength (and hence magnetic flux density) right outside of the major axis of the coil. Again, careful placement and sizing off magnetic sources and sinks (i.e. "north" and "south" poles) can be used to carefully control the manipulation of magnetic particles in the lysis tube. Furthermore, the size of the permanent ferromagnets and the size of the non-magnetic collision boundaries may be varied to optimize lysis conditions for a specific organism or sample-type. For instance, the non-magnetic collision beads can be selected to have diameters that are a couple order larger or smaller than the organism of interest. Optimization of the bead size can also allow achievement of better lysis yields.

EXAMPLES

The mechanical lysis arrangement of several embodiments herein described is further illustrated in the following examples, which are provided by way of illustration and are not intended to be limiting.

Example 1

Lysis of Yeast Cells Using the Mechanical Lysis Arrangement

Testing of the mechanical lysis arrangement as described in Example 1 was performed using *Saccharomyces cerevisiae* (baker's yeast). This organism is well-studied, providing an excellent model for the characterization of the mechanical lysis arrangement. In addition, the organism has a tough cell wall that is more difficult to break down than most eukaryotic cell walls. Thus, it serves as an excellent benchmark for the performance of the mechanical lysis arrangement.

Figure 10:
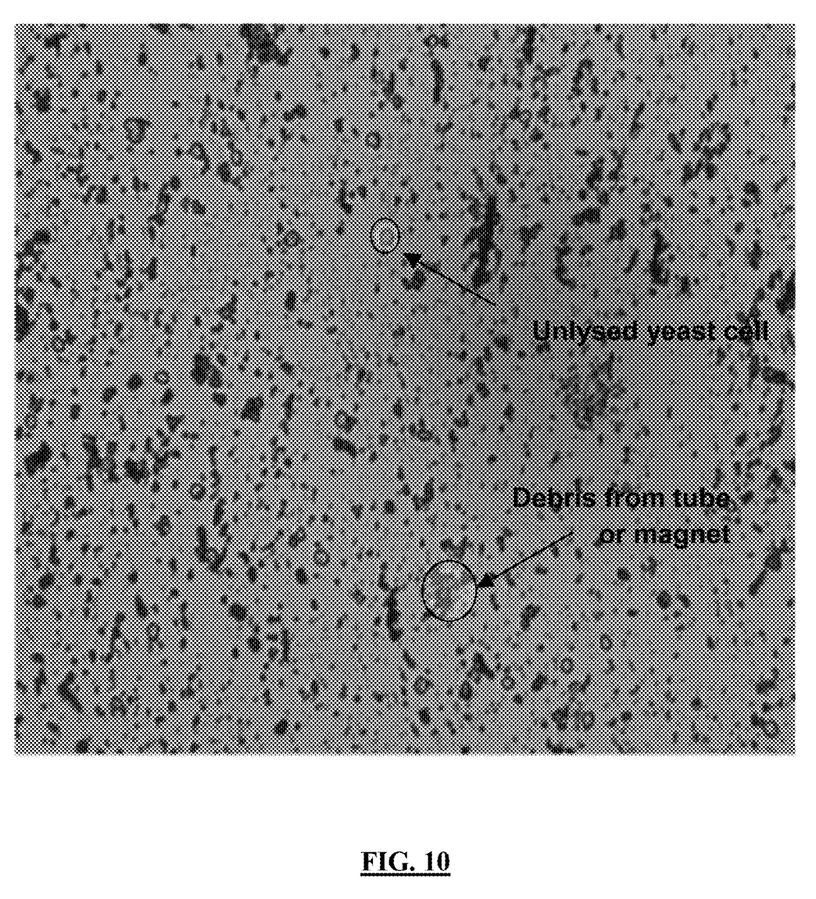
FIG. 10 shows a micrograph depicting results of a cell lysis experiment using the mechanical lysis arrangement according to several embodiments.

To lyse cells, an aliquot of yeast cells suspended in phosphate buffered saline (PBS) was loaded into a lysis tube (10) containing glass beads (lysis aids; 50) and two NeFeB permanent magnets (30). The device was powered using 120V, 60 Hz AC power from a wall outlet. The arrangement was run for 1 minute followed by 1 minute of no activity to prevent over-heating of the sample. This 1 minute on/one minute off protocol was run for 15 minutes total. The results show that this 15 minutes lysis protocol is sufficient to destroy almost all the cells in the yeast sample. FIG. 10 shows a representative micrograph of the cell lysate viewed under a microscope after running the experiment. With the exception of a few live cells, nearly all cells were effectively lysed using the arrangement as described above.

Example 2

Comparison of Lysis Efficiency Using the Mechanical Lysis Arrangement of Several Embodiments with Other Methods of Lysis An additional experiment was conducted to compare the efficiency of lysis between the method used by the mechanical lysis arrangement of the present disclosure of several embodiments and a method of lysis known in the art. In particular, a device produced by Precellys Inc. was compared to lysis by the mechanical lysis arrangement of the present disclosure.

Figure 11:
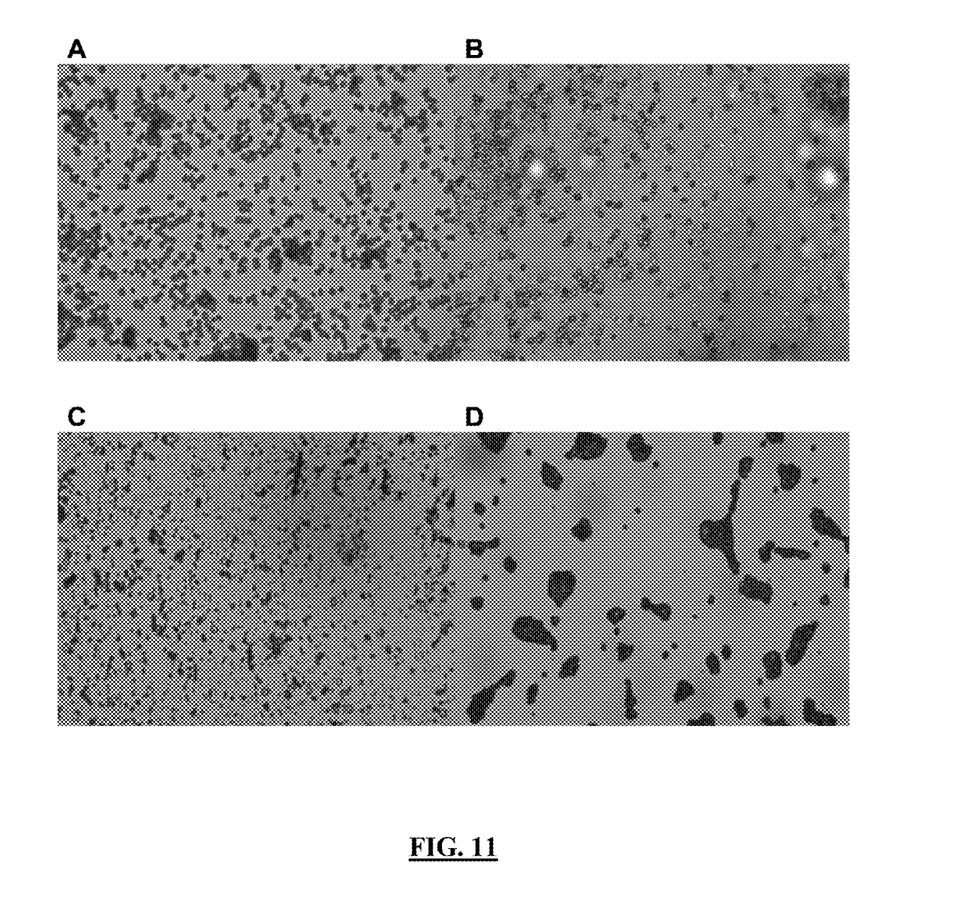

Four samples were prepared in order to qualitatively compare cell lysis efficiency. Each sample was prepared as described below and the contents of the sample were imaged using a microscope as in Example 1. The first sample is an unlysed control sample of yeast stock solution that was not subjected to any lysis procedure. A representative micrograph of this sample is depicted in FIG. 11, Panel A. The second sample (depicted in FIG. 11, Panel B) is a sample of yeast cells that was lysed using the mechanical lysis arrangement of several embodiments, but the lysis procedure was conducted continually for 15 minutes without interruption. The third sample (depicted in FIG. 11, Panel C) is a sample of yeast cells that were lysed using the mechanical lysis arrangement of several embodiments using a protocol wherein the lysis arrangement was operated for one minute then was turned off for one minute. This pattern (one minute on, one minute off) was repeated for a total of 15 minutes followed by analysis of the lysate. The fourth sample (depicted in FIG. 11, Panel D) is a sample of yeast cells that were lysed using a procedure according to Precellys Inc. In particular, this lysis was conducted according to the instructions in a Precellys yeast-lysis kit VK05. The results show that the best lysis, according to the experimental results, was achieved using the one minute on/one minute off procedure using the mechanical lysis arrangement of the present disclosure.

The examples set forth above are provided to give those of ordinary skill in the art a complete disclosure and description of how to make and use the embodiments of the mechanical lysis arrangement and methods of the disclosure, and are not intended to limit the scope of what the inventors regard as their disclosure. Modifications of the above-described modes for carrying out the disclosure that are obvious to persons of skill in the art are intended to be within the scope of the following claims.

It is to be understood that the disclosures are not limited to particular technical applications or fields of study, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Although any methods and materials similar or equivalent to those described herein can be used in the practice for testing of the specific examples of appropriate materials and methods are described herein.

What is claimed is:

1. A method to lyse a biological sample, comprising placing the biological sample and at least one permanent magnet inside a lysis tube, and generating a magnetic field, the magnetic field accelerating the at least one permanent magnet towards the biological sample for a time and under conditions sufficient to cause the biological sample to be lysed, wherein the at least one permanent magnet is sized to be substantially restricted to motion along an axis the lysis tube, the motion occurring when the magnetic field is generated.

2. The method according to claim 1, further comprising providing a plurality of lysis aids together with the biological sample inside the lysis tube.

3. The method according to claim 2, wherein the plurality of lysis aids are made from a material selected from the group consisting of glass, silica, iron, graphite, and plastic.

4. The method according to claim 1, wherein the at least one permanent magnet is at least two permanent magnets and the at least one electromagnet is at least two electromagnets.

5. The method according to claim 1, wherein magnetic field strength generated by the at least one electromagnet is between 0.003 and 10 Tesla.

6. The method according to claim 1, wherein the magnetic field is generated by the at least one electromagnet by passing alternating current through the electromagnet, the current being of 120 volts and alternating at a frequency of 60 Hz.

7. The method according to claim 1, wherein the magnetic field is generated through at least one electromagnet.

* * * * *